(12) United States Patent
Goravar et al.

(10) Patent No.: US 8,511,144 B2
(45) Date of Patent: Aug. 20, 2013

(54) TORSIONAL SENSOR, METHOD THEREOF, AND SYSTEM FOR MEASUREMENT OF FLUID PARAMETERS

(75) Inventors: Shivappa Ningappa Goravar, Bangalore (IN); Edward Randall Furlong, Beverly, MA (US); Manoj Kumar Koyithitta Meethal, Bangalore (IN); Vamshi Krishna Reddy Kommareddy, Bangalore (IN); Baskaran Ganesan, Bangalore (IN); Xiaolei Shirley Ao, Lexington, MA (US)

(73) Assignee: General Electric Company, Niskayuna, NY (US)

( * ) Notice: Subject to any disclaimer, the term of this patent is extended or adjusted under 35 U.S.C. 154(b) by 718 days.

(21) Appl. No.: 12/685,388

(22) Filed: Jan. 11, 2010

(65) Prior Publication Data

US 2011/0167906 A1 Jul. 14, 2011

(51) Int. Cl.
*G01N 9/00* (2006.01)
(52) U.S. Cl.
USPC ........................................ 73/32 A; 73/861.18
(58) Field of Classification Search
USPC ................. 73/32 A, 54.41, 61.49, 861.18
See application file for complete search history.

(56) References Cited

U.S. PATENT DOCUMENTS

| 4,193,291 | A | | 3/1980 | Lynnworth |
| 4,893,496 | A | | 1/1990 | Bau et al. |
| 5,020,380 | A | * | 6/1991 | Keita ........................ 73/861.357 |
| 6,912,918 | B1 | * | 7/2005 | Lynnworth et al. ......... 73/861.26 |
| 7,254,987 | B2 | * | 8/2007 | Tinianov et al. .............. 73/32 A |
| 7,665,357 | B2 | * | 2/2010 | Mueller et al. .............. 73/290 V |

OTHER PUBLICATIONS

Z. Fan, M.J.S. Lowe, M. Castaings, C. Bacon; "Propagation of Torsional Waves in a Waveguide of Arbitrary Cross-section Immersed in a Fluid"; 17th World Conference on Nondestructive Testing, Oct. 25-28, 2008, Shanghai, China; 8 Pages.

* cited by examiner

*Primary Examiner* — Max Noori
(74) *Attorney, Agent, or Firm* — Jason K. Klindtworth

(57) ABSTRACT

A torsional sensor for sensing at least one parameter of a fluid is disclosed. The torsional sensor includes a torsional portion coupled to a reference portion and including a plurality of projections extending outward and spaced apart from each other. At least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid.

44 Claims, 12 Drawing Sheets

TORSIONAL SENSOR, METHOD THEREOF, AND SYSTEM FOR MEASUREMENT OF FLUID PARAMETERS

BACKGROUND

The invention relates generally to a torsional sensor used for measurement of at least one parameter of a fluid by the propagation of torsional wave energy along the torsional sensor located partially in contact with the fluid.

In industrial process control, it is often required to determine at least one parameter attributed to fluids along flow paths, for example in pipes. The parameters may include density of the fluid, fluid velocity, fluid level, temperature, fluid phase, or the like. There are a number of known sensors, which are used for detection of parameters associated with the fluids.

One such sensor used for detection of parameters associated with the fluids is a torsional sensor. In such a device, the torsional sensor is partially inserted into the fluid whose property needs to be measured. Wave energy is guided along the sensor held partially in contact with the fluid. The parameter of the fluid surrounding the torsional sensor influences the torsional wave characteristics, specifically the time of flight of the wave mode. In other words, the interaction of the guided wave energy along the sensor with the fluid results in a lower velocity of propagation of the guided wave energy along the sensor, so that the change in flight time of the wave, as compared to a reference time with the sensor in air or vacuum, provides an indication of a parameter of the fluid in contact with the sensor. In particular circumstances, where at least one of the fluid composition, container geometry and sensor characteristics are known, a measurement of flight time of the wave energy guided along the sensor may provide an indication of a parameter of the fluid. However, none of the known torsional sensor designs results in an improvement in measurement of at least one parameter through a longer time of flight for a given wave mode. Moreover, the known torsional sensor designs are not suitable for measurement of at least one parameter of different type of fluids, specifically, one phase fluid, two-phase fluid mixture, and multi-phase fluid mixture.

As a result, there is a continued need for an improved torsional sensor that addresses at least one of these and other shortcomings.

BRIEF DESCRIPTION

In accordance with one exemplary embodiment of the present invention, a torsional sensor for sensing at least one parameter of a fluid is disclosed. The torsional sensor includes a torsional portion coupled to a reference portion and including a plurality of projections extending outward and spaced apart from each other. At least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid.

In accordance with another exemplary embodiment of the present invention, a sensing system for sensing at least one parameter of a fluid is disclosed. The sensing system includes a torsional sensor having a torsional portion coupled to a reference portion and including a plurality of projections extending outward and spaced apart from each other. An excitation device is configured to excite a wave energy in the torsional sensor. At least a portion of the torsional sensor is mountable for immersion in the fluid and operable to propagate the wave energy that interacts with the fluid along the at least portion of the torsional sensor so as to affect propagation of the wave energy in a manner dependent on the at least one parameter of the fluid. A transducer device is configured to provide torsional excitation to the torsional sensor and detect wave energy from the torsional portion. A processor device is configured to determine at least one parameter of the fluid in response to an output from the transducer device.

In accordance with one exemplary embodiment of the present invention, a torsional sensor for sensing at least one parameter of a fluid is disclosed. The torsional sensor includes a reference portion having at least one notch.

In accordance with another exemplary embodiment of the present invention, a torsional sensor for sensing at least one parameter of a fluid is disclosed. The sensor includes a reference portion including a first material. A torsional portion is coupled to the reference portion and includes a plurality of projections extending outward and spaced apart from each other. The torsional portion includes a second material different from the first material.

In accordance with another exemplary embodiment of the present invention, a torsional sensor for sensing at least one parameter of a fluid is disclosed. The sensor includes a reference portion having at least one notch dividing the reference portions into two or more sub-sections. A torsional portion is coupled to the reference portion and having a plurality of projections extending outward and spaced apart from each other. The reference portion and the torsional portion include same material.

In accordance with another exemplary embodiment of the present invention, a method for sensing at least one parameter of a fluid is disclosed.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed herein below, embodiments of the present invention discloses a torsional sensor for sensing at least one parameter of a fluid. The torsional sensor includes a reference portion and a torsional portion coupled to the reference portion. The torsional portion includes a plurality of projections extending outward and spaced apart from each other. The aspect ratio of the torsional portion may be varied. The aspect ratio may be in the range of but not limited to 1:2 to 1:7. At least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid. The at least one parameter include absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid. The fluid may include a single-phase fluid, or a two-phase fluid mixture, or a multi-phase fluid mixture. In a specific embodiment, a system incorporating the torsional sensor is disclosed. The exemplary torsional sensor design provides substantial improvement in resolution for measurement of at least one parameter of a single-phase fluid, or a two-phase fluid mixture, or a multi-phase fluid mixture.

Figure 1:
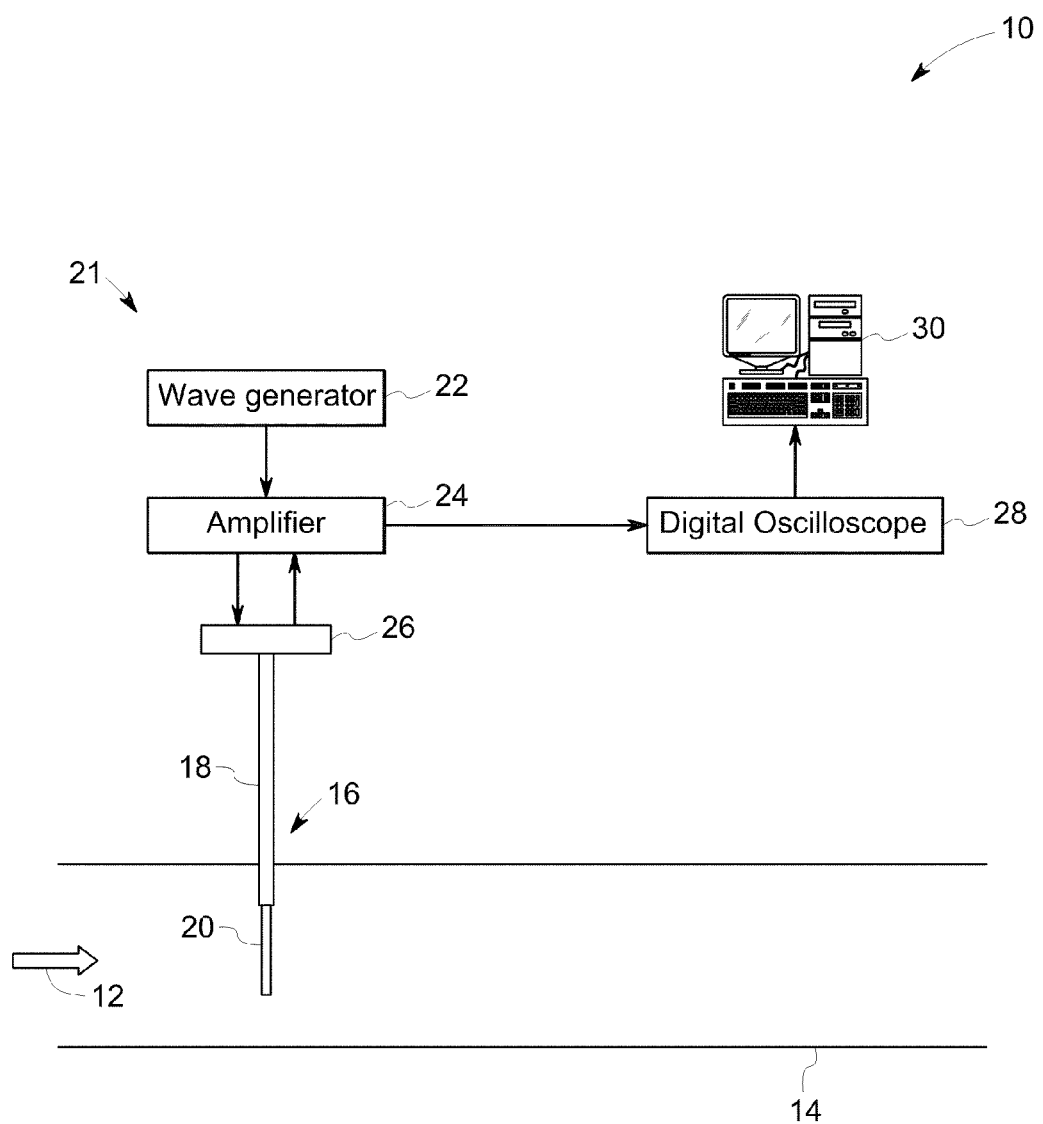
FIG. 1 is a block diagram of a sensing system for sensing at least one parameter of a fluid flowing through a conduit in accordance with an exemplary embodiment of the present invention.

Referring to FIG. 1, a block diagram of a sensing system 10 for sensing at least one parameter of a fluid 12 flowing through a conduit 14 is illustrated. In the illustrated embodiment and subsequent embodiments, the conduit may be a vertical arrangement or a horizontal arrangement. It should be noted that even though a conduit is disclosed, the sensing system 10 is applicable to any device containing a fluid for sensing at least one parameter attributed to the fluid in both static and flowing conditions. The system 10 includes a torsional sensor 16 partially immersed in the fluid 12 flowing through the conduit 14. The torsional sensor 16 includes a reference portion 18 and a torsional portion 20. In a specific embodiment, the reference portion 18 is a cylindrical-shaped reference portion. The depth of the torsional sensor 16 immersed in the fluid 12 may be varied.

The system 10 further includes an excitation device 21 having a wave generator 22 configured to transmit shear wave energy via an amplifier 24 to the torsional sensor 16. A transducer device 26 is configured to provide shear excitation to the torsional sensor 16. The ultrasonic guided wave, which propagates along the torsional sensor 16, detects the presence and nature of the surrounding fluid 12. When the torsional sensor 16 is partially immersed in the fluid 12, the propagation of wave is affected by at least one parameter of the fluid 12. Hence at least one parameter of the fluid 12 can be measured by detecting the propagation of wave energy along the sensor 16. At least one parameter includes absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid 12. The fluid 12 may include a single-phase fluid, or a two-phase fluid mixture, or a multi-phase fluid mixture. It should be noted herein that a two-phase fluid mixture, or a multi-phase fluid mixture might include two or more fluids having different densities. For example, a multi-phase fluid mixture may include oil, water, and gas. The excitation source and receiver may be, piezoelectric, curved piezoelectric, phased array magneto strictive, Laser-based electromagnetic acoustic transducer (EMAT), phased EMAT and Membrane. The application of the exemplary sensor 16 to all such types of fluid is envisaged.

In the illustrated embodiment, the transducer device 26 is also configured to detect the wave energy from the torsional portion 20 of the sensor 16. A corresponding output signal from the transducer device 26 is fed via a digital oscilloscope 28 to a processor device 30, for example, a computer. The processor device 30 is configured to determine at least one parameter of the fluid 12 in response to the output signal from the transducer device 30. It should be noted herein that the configuration of the sensing system 10 is an exemplary embodiment and should not construed in any way as limiting the scope of the invention. The exemplary sensor 16 is applicable to any application requiring detection of at least one parameter attributed to the fluid 12 in which the fluid is contained in a vessel or flowing through a conduit. Typical examples include petroleum industry, oil & gas, or the like. The exemplary sensor design and arrangement of sensors are explained in greater detail with reference to subsequent embodiments.

Figure 2:
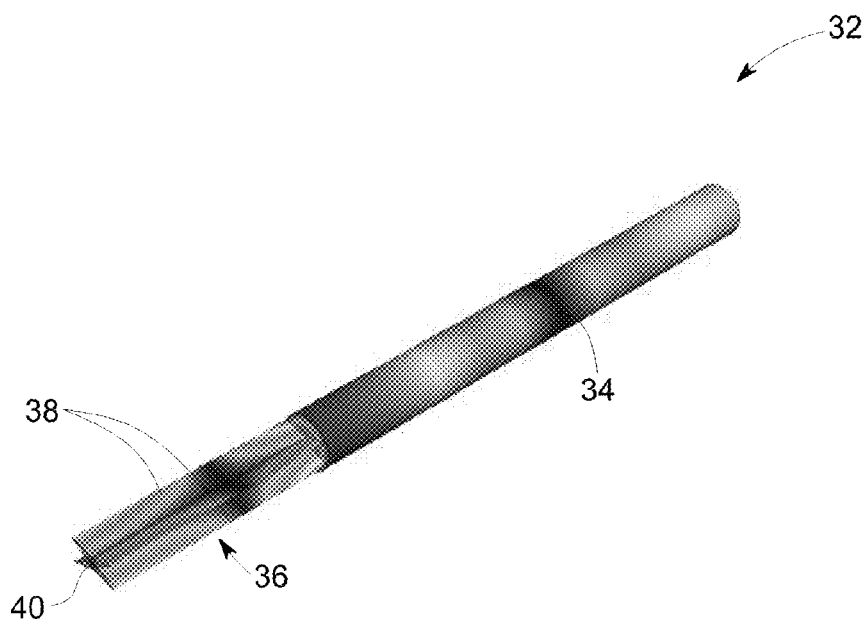
FIG. 2 is a perspective view of an exemplary torsional sensor in accordance with an exemplary embodiment of the present invention.

Referring to FIG. 2, a perspective view of an exemplary torsional sensor 32 is illustrated. The torsional sensor 32 includes a reference portion 34 and a torsional portion 36. In the illustrated embodiment, the reference portion 34 is a cylindrical-shaped reference portion and the torsional portion 36 is a X-shaped torsional portion. The torsional portion 36 includes a plurality of projections 38 extending outward extending outward and spaced apart from each other. Specifically, the torsional portion 36 includes the plurality of individual projections 38 disposed symmetrically about a center section 40 of the torsional portion 36.

As discussed previously, the torsional sensor 32 utilizes change in speed of wave energy propagating along the torsional portion 36 due to the presence of surrounding fluid medium to detect at least one parameter of the fluid medium. As the shear wave propagates through the torsional portion 36 of the sensor 32, acceleration and deceleration of fluid surrounding the torsional portion 36 occurs. Normal forces are exerted on the surface of the torsional portion 36, which in turn act on the surrounding fluid. The fluid motion surrounding the torsional portion 36 is induced by the normal velocity component of velocity at a fluid-solid interface and also by the viscous drag of the surrounding fluid. As a result, the fluid is trapped at corners of the torsional portion 36 affecting the propagation of the wave energy. In other words, the propagation of the wave energy is attributed to the inertial of the surrounding fluid. At least one parameter of the surrounding fluid medium can be detected by determining speed of propagating wave energy.

Figure 3:
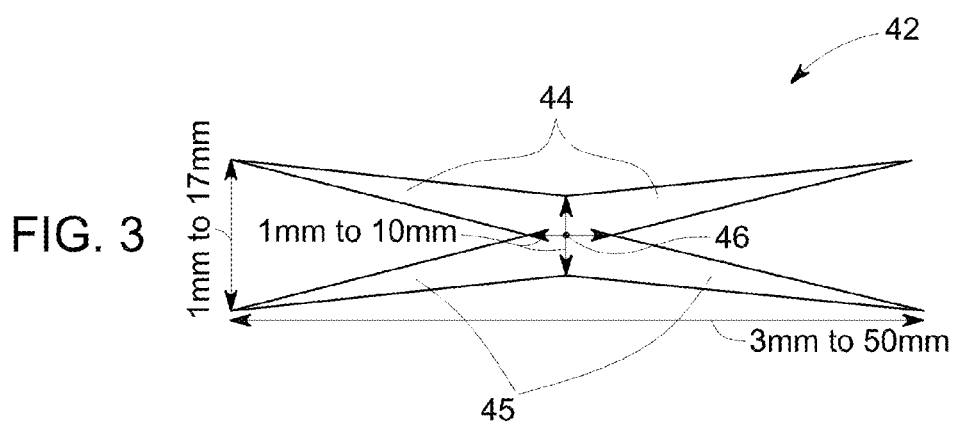
FIG. 3 is a cross-sectional view of an exemplary torsional portion in accordance with an exemplary embodiment of the present invention.

Referring to FIG. 3, a cross-sectional view of an exemplary torsional portion 42 is illustrated. The torsional portion 42 is an X-shaped torsional portion. The torsional portion 42 includes a plurality of projections 44, 45 extending outward from a center section 46 and spaced apart from each other. The plurality of projections 44, 45 are disposed symmetrically about the center section 46. In a specific embodiment, the distance between two projections 44 may be in the range of 3 mm to 50 mm. In another specific embodiment, the distance between two projections 45 may be in the range of 3 mm to 50 mm. In yet another specific embodiment, the distance between a projection 44 and another projection 45 may be in the range of 1 mm to 17 mm. The distance between opposing intersection points of the projections 44, 45 may be in the range of 1 mm to 20 mm.

Figure 4:
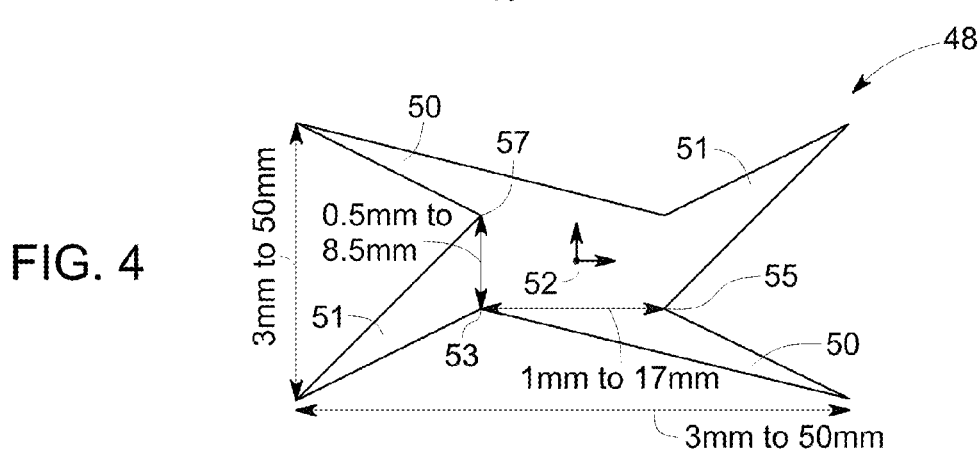
FIG. 4 is a cross-sectional view of an exemplary torsional portion in accordance with an exemplary embodiment of the present invention.

Referring to FIG. 4, a cross-sectional view of an exemplary torsional portion 48 is illustrated. The torsional portion 48 is an X-shaped torsional portion The torsional portion 48 includes a plurality of projections 50, 51 extending outward from a center section 52 and spaced apart from each other. The plurality of projections 50, 51 are disposed asymmetrically about the center section 52. The distance between the projections 50, 51 may be in the range of 3 mm to 50 mm. The distance between the intersections points 53, 55 may be in the range of 1 mm to 17 mm. The distance between the intersection points 53, 57 may be in the range of 0.5 mm to 8.5 mm.

Figure 5:
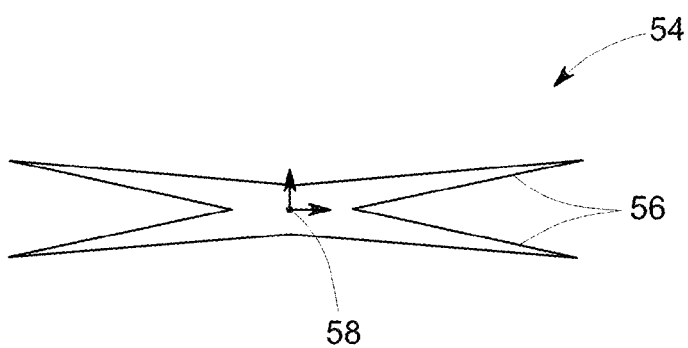
FIG. 5 is a cross-sectional view of an exemplary torsional portion in accordance with an exemplary embodiment of the present invention.

Referring to FIG. 5, a cross-sectional view of an exemplary torsional portion 54 is illustrated. The torsional portion 54 is an X-shaped torsional portion The torsional portion 54 includes a plurality of projections 56 extending outward from a center section 58 and spaced apart from each other. The plurality of projections 56 are disposed symmetrically about the center section 58.

Figure 6:
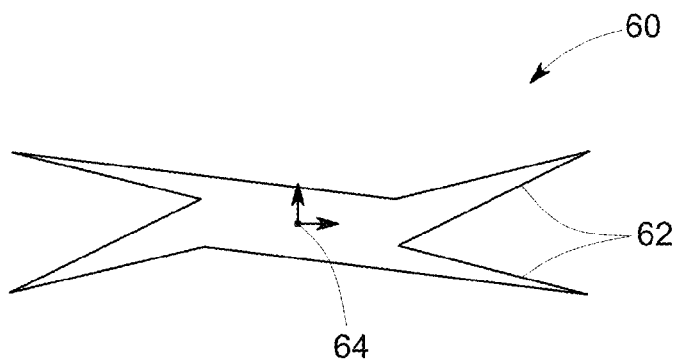
FIG. 6 is a cross-sectional view of an exemplary torsional portion in accordance with an exemplary embodiment of the present invention.

Referring to FIG. 6, a cross-sectional view of an exemplary torsional portion 60 is illustrated. The torsional portion 42 is an X-shaped torsional portion The torsional portion 60 includes a plurality of projections 62 extending outward from a center section 64 and spaced apart from each other. The plurality of projections 62 are disposed symmetrically asymmetrically about the center section 64.

Figure 7:
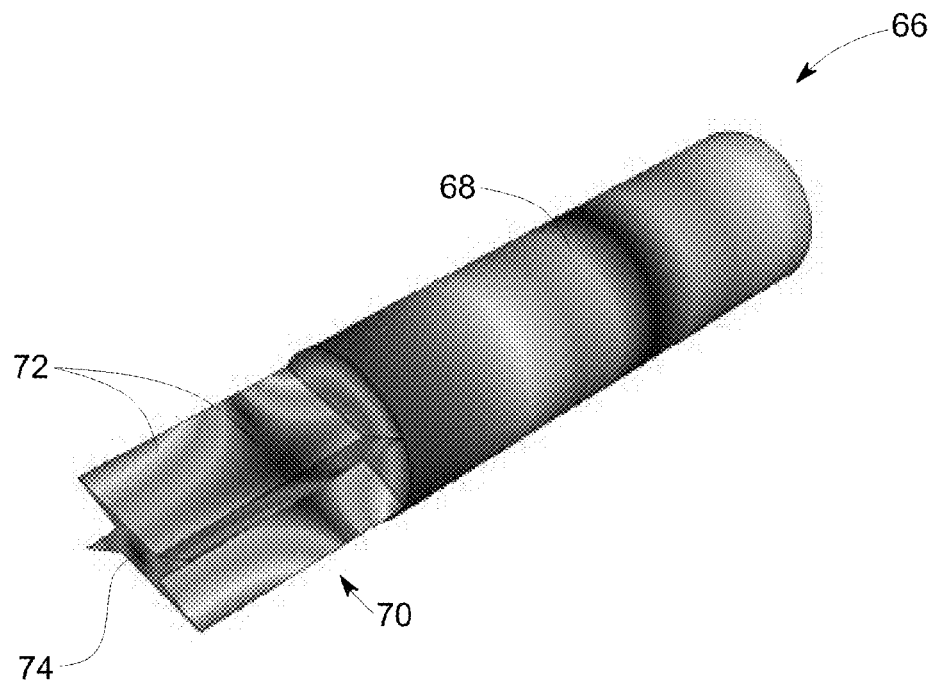
FIG. 7 is a perspective view of an exemplary torsional sensor in accordance with an exemplary embodiment of the present invention.

Referring to FIG. 7, a perspective view of an exemplary torsional sensor 66 is illustrated. The torsional sensor 66 includes a reference portion 68 and a torsional portion 70. In the illustrated embodiment, the reference portion 68 is a cylindrical-shaped reference portion and the torsional portion 70 is a fan-shaped torsional portion. The torsional portion 70 includes one projection 72 extending outwards or a plurality of projections 70 extending outward and spaced apart from each other. Specifically, the torsional portion 70 includes the plurality of individual projections 72 disposed symmetrically about a center section 74 of the torsional portion 70.

Figure 8:
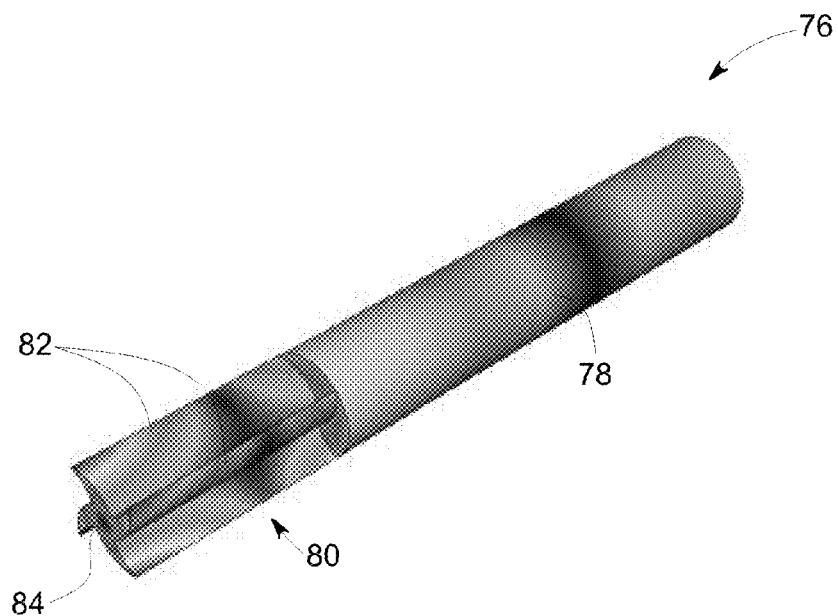
FIG. 8 is a perspective view of an exemplary torsional sensor in accordance with an exemplary embodiment of the present invention.

Referring to FIG. 8, a perspective view of an exemplary torsional sensor 76 is illustrated. The torsional sensor 76 includes a reference portion 78 and a torsional portion 80. In the illustrated embodiment, the reference portion 78 is a cylindrical-shaped reference portion and the torsional portion 80 is a curved fan-shaped torsional portion. The torsional portion 80 includes one projection 82 extending outward or a plurality of projections 80 extending outward and spaced apart from each other. Specifically, the torsional portion 80 includes the plurality of individual projections 82 disposed symmetrically about a center section 84 of the torsional portion 80.

Figure 9:
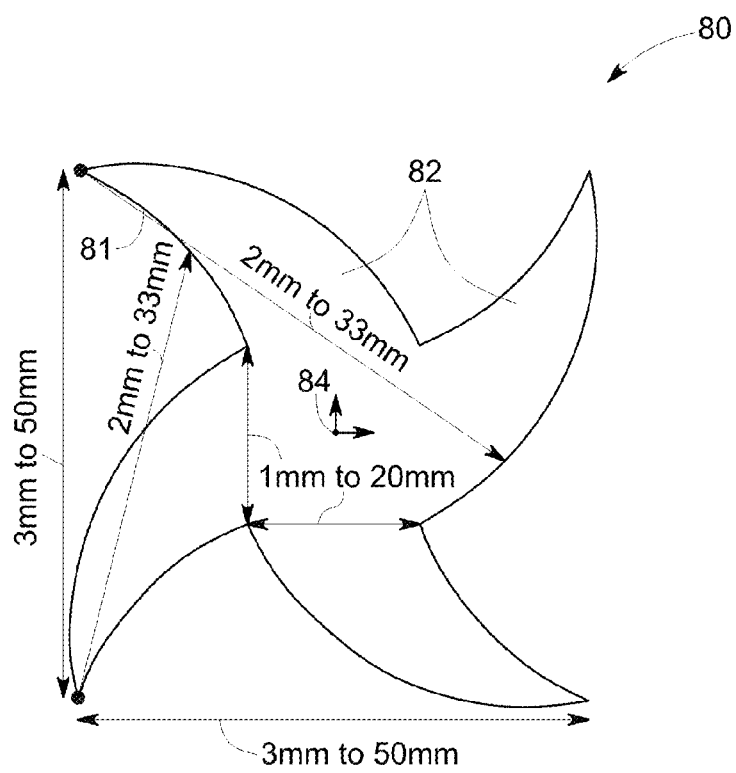
FIG. 9 is a cross-sectional view of an exemplary torsional portion in accordance with the exemplary embodiment of FIG. 8.

Referring to FIG. 9, a cross-sectional view of the torsional portion 80 is illustrated. The torsional portion 80 includes the plurality of individual projections 82 disposed symmetrically about a center section 84 of the torsional portion 80. The distance from a tip of one projection 82 to a tip of the adjacent projection 80 may be in the range of 3 mm to 50 mm. The base of each projection 80 has a length in the range of 1 mm to 20 mm. The distance from the tip of each projection 80 to a curvature portion 81 of the adjacent projection 80 may be in the range of 2 mm to 33 mm.

Figure 10:
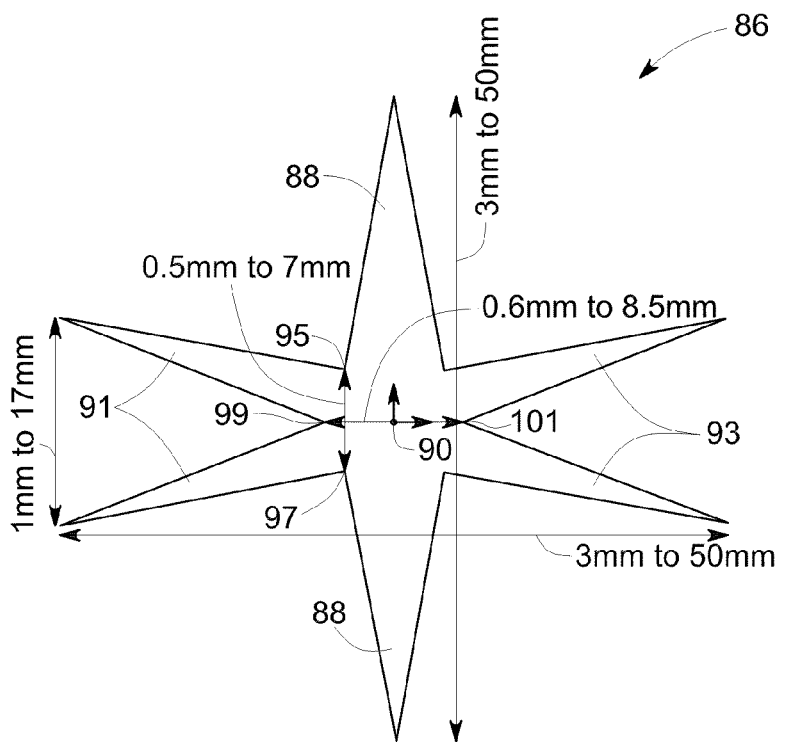
FIG. 10 is a cross sectional view of an exemplary torsional portion in accordance with an exemplary embodiment of the present invention.

Referring to FIG. 10, a cross-sectional view of an exemplary star shaped torsional portion 86 is illustrated. The torsional portion 86 includes a plurality of projections 88, 91, 93 extending outward from a center section 90 and spaced apart from each other. The plurality of projections 88, 91, 93 are disposed symmetrically about the center section 90. In one embodiment, the distance between tips of two projections 88 may be in the range of 3 mm to 50 mm. In another specific embodiment, the distance between tips of two projections 91 may be in the range of 1 mm to 17 mm. In yet another specific embodiment, the distance between a tip of one projection 91 and a tip of the projection 93 may be in the range of 3 mm to 50 mm. In yet another embodiment, the distance between intersection points 95, 97 may be in the range of 0.5 mm to 7 mm. In another specific embodiment, the distance between intersection points 99, 101 may be in the range of 0.6 mm to 8.5 mm.

It should be noted herein that the dimensions disclosed in the embodiments discussed above are exemplary values and should not be construed in any way as limiting the scope of the invention.

Figure 11:
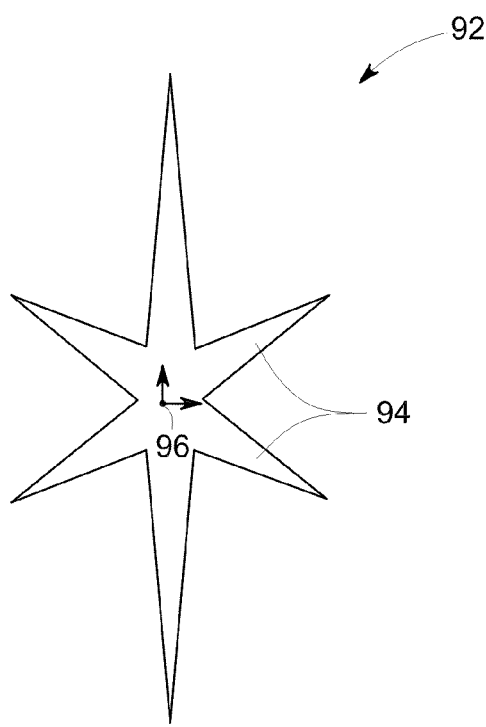
FIG. 11 is a cross sectional of an exemplary torsional portion in accordance with an exemplary embodiment of the present invention.

Referring to FIG. 11, a cross-sectional view of an exemplary star shaped torsional portion 92 is illustrated. The torsional portion 92 includes a plurality of projections 94 extending outward from a center section 96 and spaced apart from each other. The plurality of projections 94 are disposed symmetrically about the center section 96.

Figure 12:
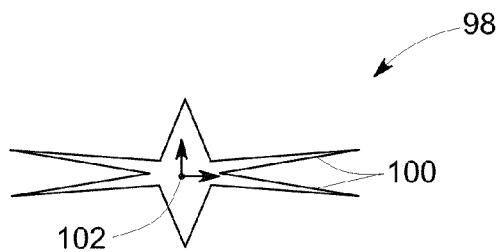
FIG. 12 is a cross sectional view of an exemplary torsional portion in accordance with an exemplary embodiment of the present invention.

Referring to FIG. 12, a cross-sectional view of an exemplary star shaped torsional portion 98 is illustrated. The torsional portion 98 includes a plurality of projections 100 extending outward from a center section 102 and spaced apart from each other. The plurality of projections 100 are disposed symmetrically about the center section 102.

Figure 13:
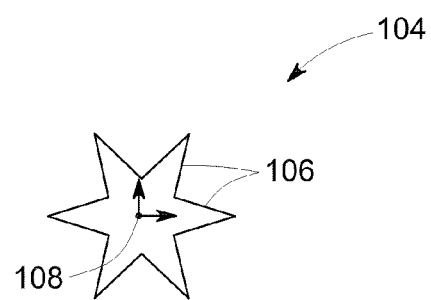
FIG. 13 is a cross sectional view of an exemplary torsional portion in accordance with an exemplary embodiment of the present invention.

Referring to FIG. 13, a cross-sectional view of an exemplary star torsional portion 104 is illustrated. The torsional portion 104 includes a plurality of projections 106 extending outward from a center section 108 and spaced apart from each other. The plurality of projections 106 are disposed symmetrically about the center section 108.

Figure 14:
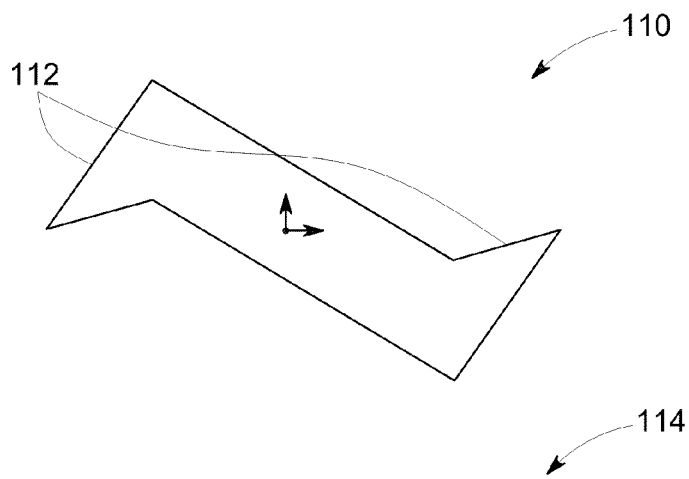
FIG. 14 is a cross sectional view of an exemplary torsional portion in accordance with an exemplary embodiment of the present invention.

Referring to FIG. 14, a cross-sectional view of an exemplary torsional portion 110 is illustrated. The torsional portion 110 includes a plurality of projections 112 extending outward and spaced apart from each other.

Figure 15:
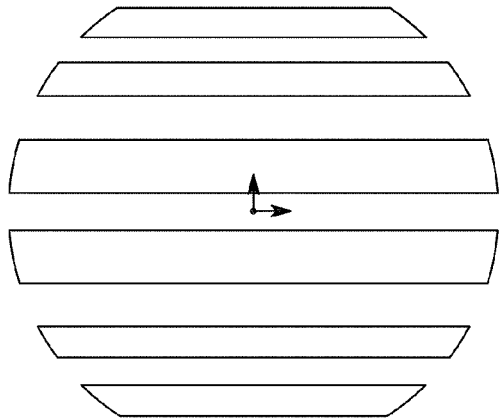
FIG. 15 is a section of an exemplary torsional portion in accordance with an exemplary embodiment of the present invention.

Referring to FIG. 15, a section 114 of an exemplary torsional portion is illustrated.

Although various shapes of the torsional portion are disclosed herein, combinations of all such shapes of the torsional portion are also envisaged.

Figure 16:
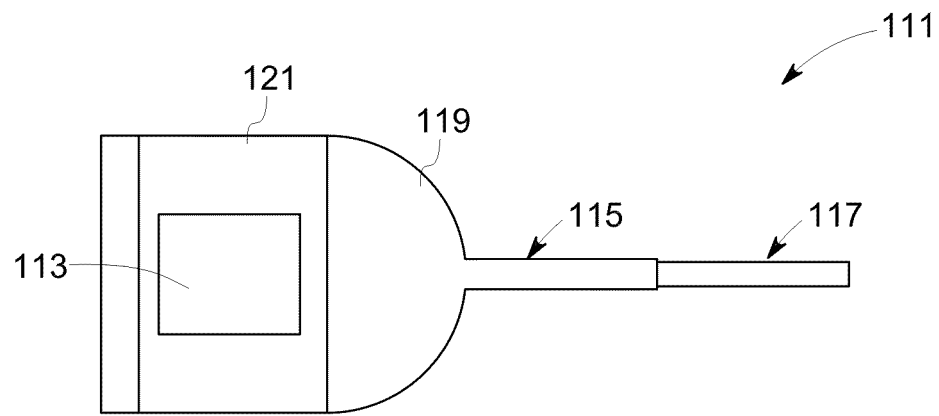
FIG. 16 is a side view of a transducer device disposed on an exemplary torsional sensor in accordance with an exemplary embodiment of the present invention.

Referring to FIG. 16, a side view of an arrangement of an exemplary sensor 111 and a transducer device 113 is illustrated. In the illustrated embodiment, the sensor 111 includes a reference portion 115 and a torsional portion 117. The reference portion 113 includes an enlarged top portion 119 having a recessed side portion 121. The transducer device 113 is mounted to the recessed side portion 121 of the reference portion 113. Such an arrangement is applicable to any of the embodiments discussed herein.

Figure 17:
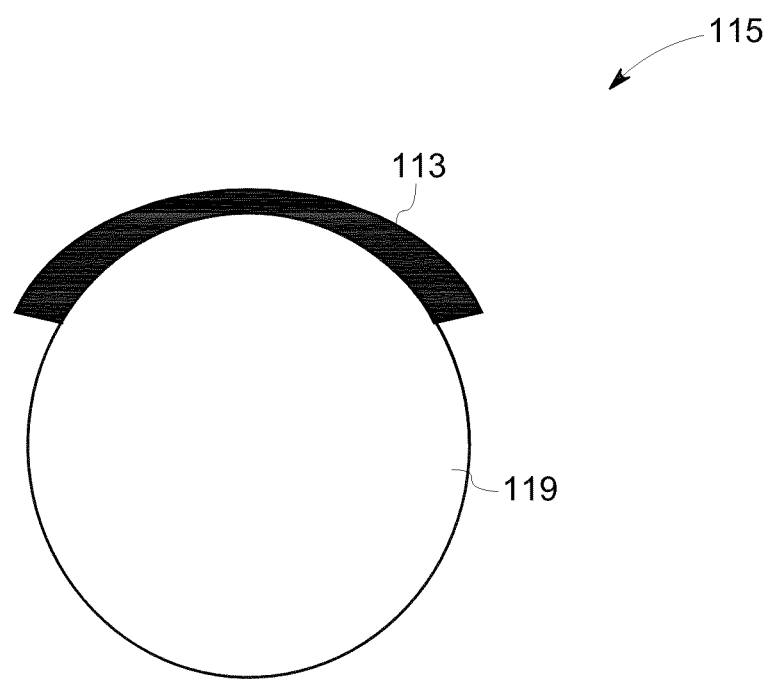
FIG. 17 is a section of a transducer device wrapped around a reference portion of an exemplary torsional sensor in accordance with an exemplary embodiment of the present invention.

Referring to FIG. 17, a side view of an arrangement of a reference portion 115 and a transducer device 113 is disclosed. The reference portion 115 includes an enlarged top portion 119 and the transducer device 113 is wrapped around the enlarged top portion 119.

Figure 18:
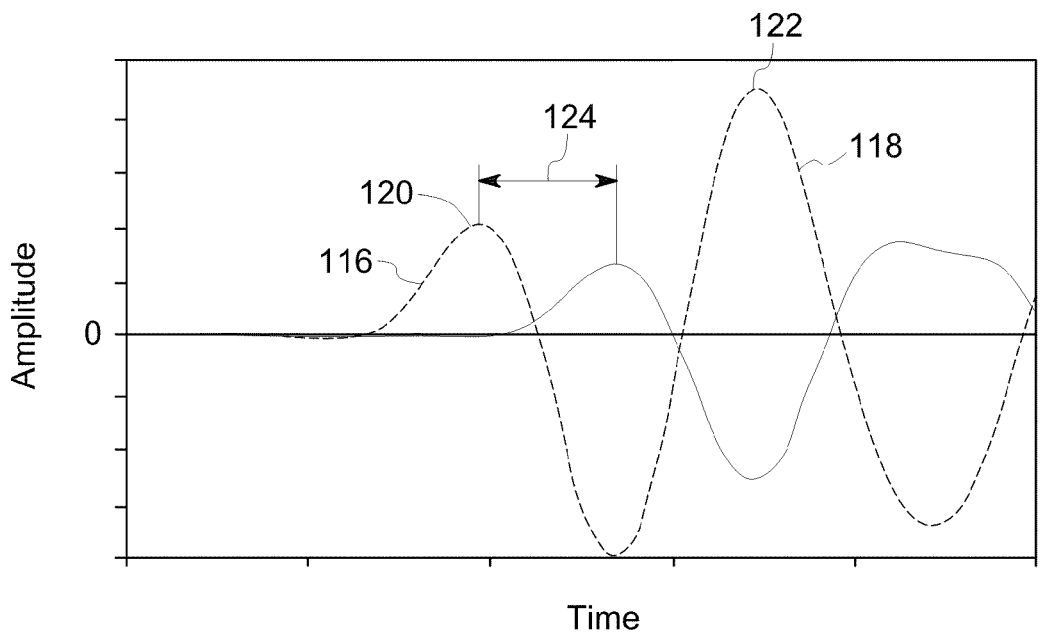
FIG. 18 is a graph representing variation of an amplitude versus time of a propagating wave along an exemplary torsional sensor in accordance with an exemplary embodiment of the present invention.

Referring to FIG. 18, a graphical representation illustrating variation in amplitude of output signals representative of wave energy from a torsional portion of a sensor with respect to time (in seconds) is illustrated. As discussed above, the transducer device is also configured to detect the wave energy from the torsional portion of the sensor. A corresponding output signal from the transducer device is fed via the digital oscilloscope to the processor device. The processor device is configured to determine at least one parameter of the fluid in response to the output signal from the transducer device.

The velocity of the propagation wave in the torsional portion is determined by measuring the time of arrival of wave at two locations of the torsional sensor. A reference signal 116 is the signal transmitted from an interface between the reference portion and the torsional portion of the sensor. Signal 118 is the signal transmitted from an end of the torsional portion of the sensor. For example, with reference to FIG. 2, a reference signal is the signal transmitted from an interface between the reference portion 34 and the torsional portion 36 of the sensor 32. The other signal is the signal transmitted from an end of the torsional portion 36 of the sensor 32. Again referring to FIG. 18, a time from a peak 120 of the reference signal 116 to a peak 122 of the signal 118 is referred to as "time of flight" 124. The velocity of the propagation wave is calculated based on the time of flight 124.

Figure 19:
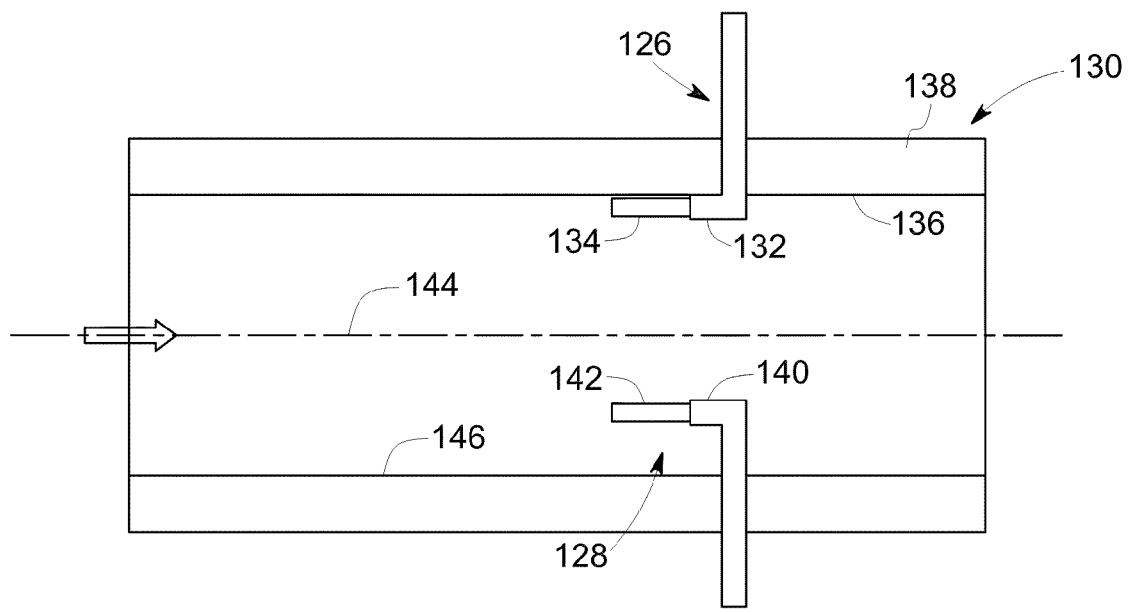
FIG. 19 is a sectional view of two torsional sensors disposed in a conduit in accordance with an exemplary embodiment of the present invention.

Referring to FIG. 19, a sectional view of an arrangement of two torsional sensors 126, 128 is illustrated. In the illustrated embodiment, the two sensors 126, 128 are disposed at different locations in a conduit 130. The sensor 126 has a reference portion 132 and a torsional portion 134. The sensor 126 is disposed proximate to one side 136 of a wall 138 of the conduit 130. The sensor 128 has a reference portion 140 and a torsional portion 142. The sensor 128 is disposed between the sensor 126 and another side 146 of the wall 138 of the conduit 130. Specifically, the sensor 128 is disposed between a central axis 144 and another side 146 of the wall 138 of the conduit 130.

In the illustrated embodiment, each sensor is subjected to a pulse echo mode of operation in which a transducer device is used for both generating and receiving the torsional wave energy. One echo corresponds to reflection of torsional wave energy from the interface between the reference portion and the torsional portion of the corresponding sensor and the other echo corresponds to reflection of torsional wave energy from an end of the corresponding sensor. In all the embodiments disclosed herein, each sensor may also subjected to a through transmission mode of operation in which one transducer device is used for generating torsional wave energy and another transducer device is used for receiving torsional wave energy.

In a specific embodiment, a two-phase fluid mixture flows through the conduit 130. For example, the two-phase fluid mixture includes oil and water. One sensor 126 is configured to detect density of one fluid, for example oil. The other sensor 128 is configured to detect density of the other fluid, for example water. In the illustrated embodiment, the sensors 126, 128 are disposed in the same location in the conduit 130. It should be noted herein that in the embodiments discussed herein, the number of sensors and the location of the sensors should not be construed as limiting. The sensor arrangement is also applicable for detection of other parameters of the fluid mixture. The sensor arrangement is also applicable for any single-phase fluid, two-phase fluid mixture, and multi-phase fluid mixture.

Figure 20:
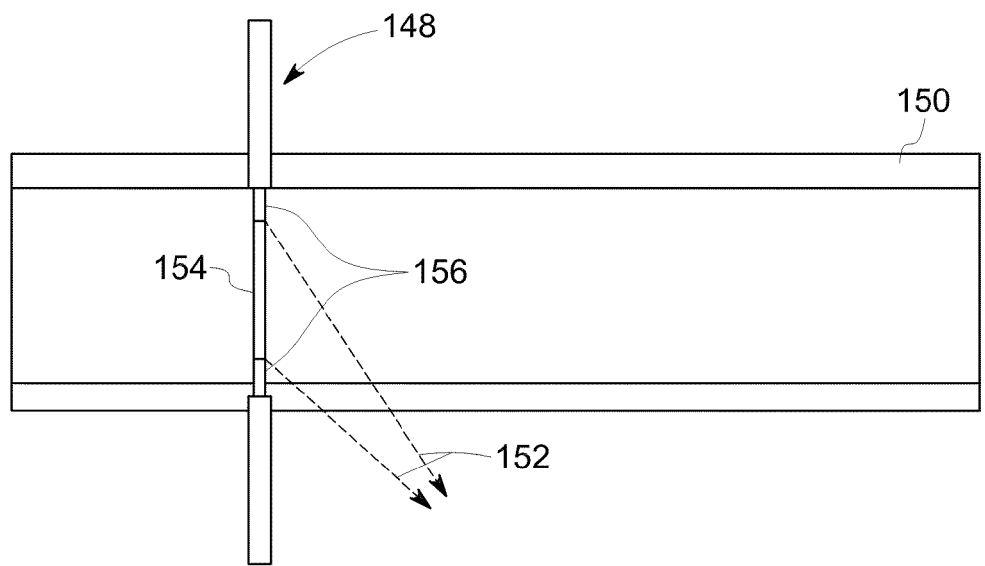
FIG. 20 is a sectional view of a torsional sensor disposed in a conduit in accordance with an exemplary embodiment of the present invention.

Referring to FIG. 20, a sectional view of an arrangement of a torsional sensor 148 is illustrated. In the illustrated embodiment, the sensor 148 is disposed in a conduit 150. In the illustrated embodiment, the sensor 148 includes a plurality of notches 152 for dividing a torsional portion 154 into a plurality of torsional sub-sections 156. The wave energy from each torsional sub-section 156 is representative of at least one parameter associated with the fluid confined to a corresponding area in the conduit 150. For example, one torsional sub-section may be indicative of density, and another sub-section may be indicative of phase fraction.

It should be noted herein that the exemplary sensor arrangement is also applicable for detection of other parameters of the fluid. The exemplary sensor arrangement is also applicable for any single-phase fluid, two-phase fluid mixture, and multi-phase fluid mixture.

Figure 21:
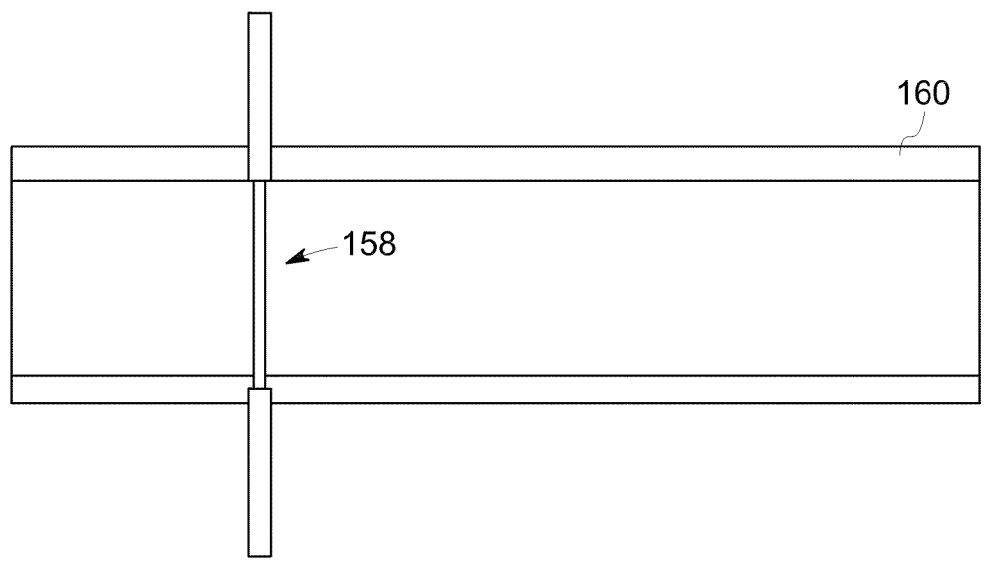
FIG. 21 is a sectional view of a torsional sensor disposed in a conduit in accordance with an exemplary embodiment of the present invention.

Referring to FIG. 21, a sectional view of an arrangement of a torsional sensor 158 is illustrated. In the illustrated embodiment, the sensor 158 is disposed extending across a diameter of a conduit 160. In one embodiment, the torsional sensor 158 is configured to detect density of a single-phase fluid. In another embodiment, the torsional sensor 158 is configured to detect an average density of a two-phase fluid mixture. In yet another embodiment, the torsional sensor 158 is configured to detect a level of each fluid phase of a multi-phase fluid mixture, when each fluid phase is confined to a corresponding area in the conduit 160. In yet another embodiment, the torsional sensor 160 is configured to detect fraction of each fluid phase of a multi-phase fluid mixture, when the phases are distributed in the conduit 160. The exemplary sensor arrangement is also applicable for detection of other parameters of a fluid/fluid mixture. The exemplary sensor arrangement is also applicable for any single-phase fluid, two-phase fluid mixture, and multi-phase fluid mixture.

Figure 22:
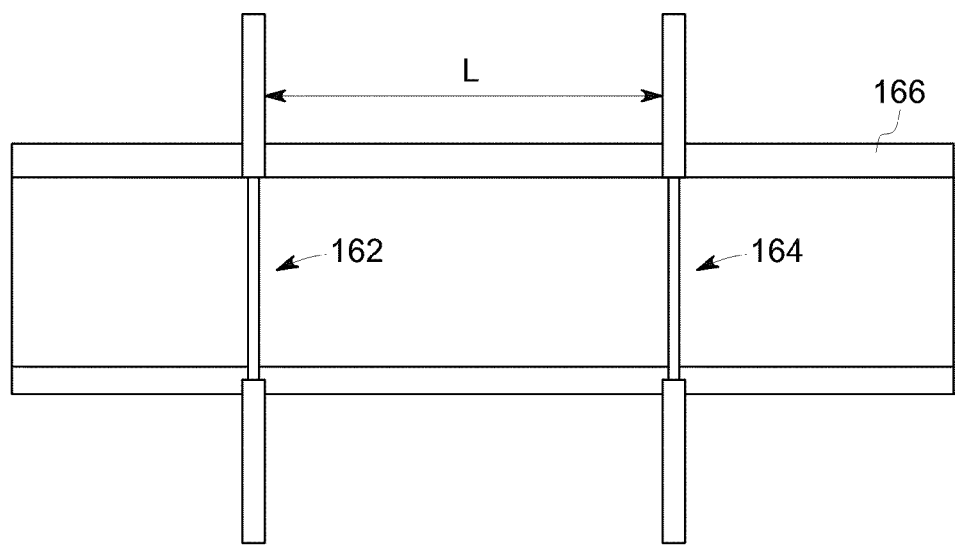
FIG. 22 is a sectional view of two torsional sensors disposed in a conduit in accordance with an exemplary embodiment of the present invention.

Referring to FIG. 22, a sectional view of an arrangement of two torsional sensors 162, 164 is illustrated. The sensors 162, 164 are disposed at different locations in a conduit 166. In the illustrated embodiment, sensors 162, 164 are spaced apart by a predetermined distance (L) in the conduit 166. In a specific embodiment, a correlation between an output response time of the sensor 162 and an output response time of the sensor 164 may be indicative of phase velocity of a fluid. For example, if an output response time of the sensor 162 is indicated by "t1" and an output response time of the sensor 164 is indicated by "t2", then phase velocity of the fluid is determined by the relation:

$$\frac{t2-t1}{L} \qquad (1)$$

As in the previous embodiments, the number of sensors and the location of the sensors should not be construed as limiting. The sensor arrangement is also applicable for detection of other parameters of a fluid/fluid mixture. The sensor arrangement is also applicable for any single-phase fluid, two-phase fluid mixture, and multi-phase fluid mixture.

Figure 23:
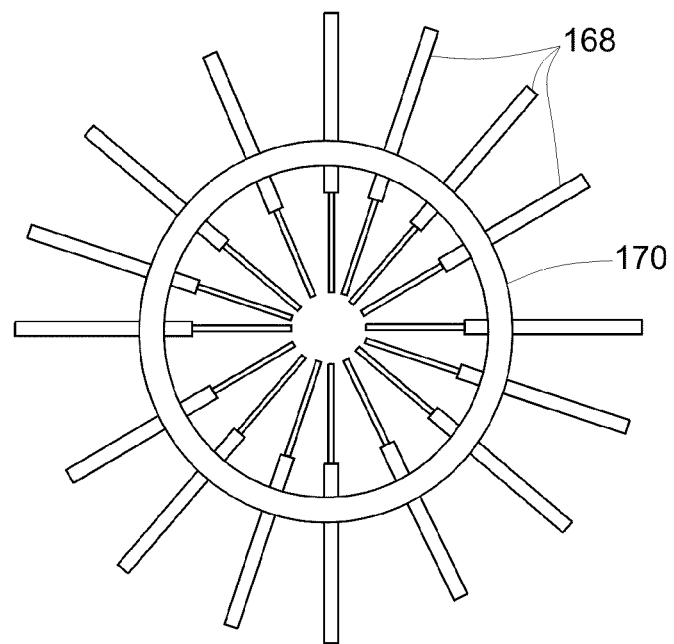
FIG. 23 is a cross sectional view of a plurality of torsional sensors disposed along a section of a conduit in accordance with an exemplary embodiment of the present invention.

Referring to FIG. 23, a cross-sectional view of an arrangement of a plurality of torsional sensors 168 is illustrated. In the illustrated embodiment, the plurality of torsional sensors 168 are disposed spaced apart from each other along a cross-section of a conduit 170. In a specific embodiment, the sensors 168 are configured to determine density profile of a two/multi-phase fluid mixture. In another embodiment, the sensors 168 are configured to determine phase fraction of each fluid phase of a two/multi-phase fluid mixture. Here again, the number of sensors should not be construed as limiting. The sensor arrangement is also applicable for detection of other parameters of the fluid mixture. The sensor arrangement is also applicable for any single-phase fluid, two-phase fluid mixture, and multi-phase fluid mixture.

Figure 24:
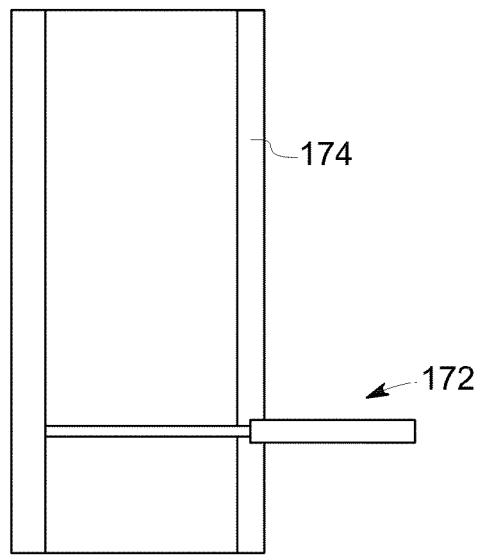
FIG. 24 is a sectional view of a torsional sensor disposed in a conduit in accordance with an exemplary embodiment of the present invention.

Referring to FIG. 24, a sectional view of an arrangement of a torsional sensor 172 is illustrated. In the illustrated embodiment, the sensor 172 is disposed extending across a conduit 174. The sensor 172 is configured to detect at least one parameter of each fluid phase of a two/multi-phase fluid mixture. In one embodiment, when a two-phase fluid mixture flows through the conduit 174, an output response of the sensor 172 at a first time may be indicative of phase density or phase fraction of one fluid phase, and another output response of the sensor at a second time later than the first time may be indicative of phase density or phase fraction of another fluid phase. The exemplary sensor arrangement is also applicable for detection of other parameters of the fluid mixture. The sensor arrangement is also applicable for any single-phase fluid, two-phase fluid mixture, and multi-phase fluid mixture.

Figure 25:
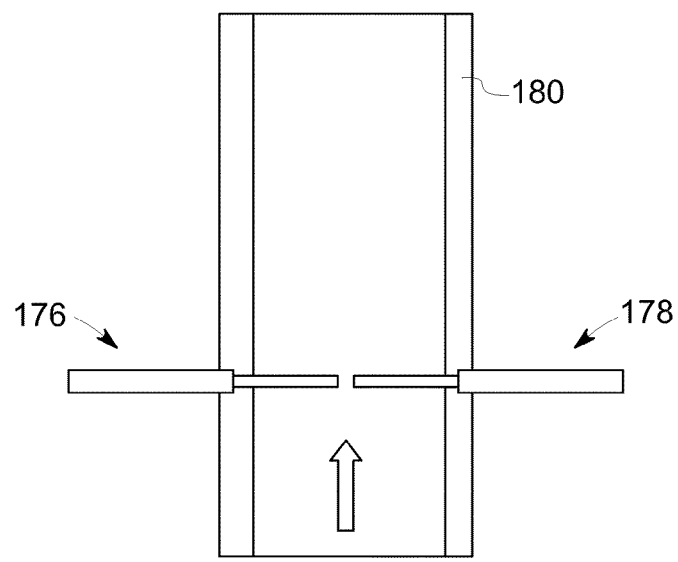
FIG. 25 is a sectional view of two torsional sensors disposed in a conduit in accordance with an exemplary embodiment of the present invention.

Referring to FIG. 25, a sectional view of an arrangement of two torsional sensors 176, 178 is illustrated. In the illustrated embodiment, the sensors 176, 178 are disposed at a same location of a conduit 180. The torsional sensor 176 has a first length and the other torsional sensor 178 has a second length different from the first length. In one embodiment, when a two-phase fluid mixture flows through the conduit 180, one sensor 176 may be configured to phase density or phase fraction of one fluid phase and the other sensor 178 may be configured to phase density or phase fraction of other fluid phase. The exemplary sensor arrangement is also applicable for detection of other parameters of the fluid mixture. The sensor arrangement is also applicable for any single-phase fluid, two-phase fluid mixture, and multi-phase fluid mixture.

Figure 26:
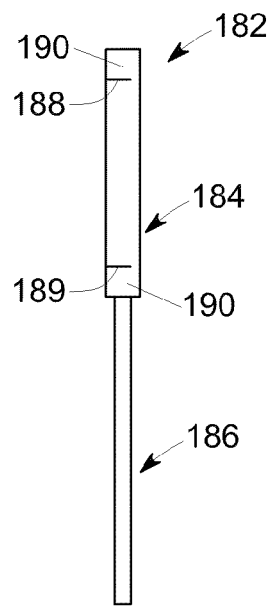
FIG. 26 is a front view of a torsional sensor in accordance with an exemplary embodiment of the present invention.

Referring to FIG. 26, a front view of an exemplary torsional sensor 182 is illustrated. The sensor 182 includes a reference portion 184 and a torsional portion 186. In the illustrated embodiment, the reference portion 184 includes two notches or grooves 188, 189 for dividing the reference portion 184 into a plurality of sub-sections 190. The reference portion 184 and the torsional portion 186 include same material. As discussed previously, the torsional sensor 182 utilizes change in speed of wave energy propagating along the torsional portion 186 due to the presence of a surrounding fluid medium to detect at least one parameter of the fluid medium.

Figure 27:
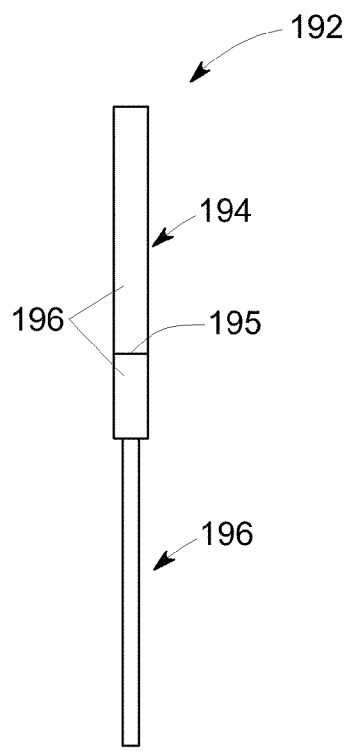
FIG. 27 is a front view of a torsional sensor in accordance with an exemplary embodiment of the present invention.

In the illustrated embodiment, the torsional portion 186 and a portion of the reference portion 184 with the notch 189 is immersed in the fluid medium. As discussed previously, the velocity of the propagation wave is calculated based on the time of flight of the propagation wave. In one embodiment, it should be noted that any variation in time of flight of the torsional wave along the torsional sensor 182 is attributed to change in at least one parameter of the fluid, for example temperature. The time of flight of the propagation wave is calibrated for a particular temperature and the time of flight is corrected based on the calibration for determining at least one parameter of the fluid. One notch 188 is a reference region corresponding to the portion of the sensor 182 exposed to air and the other notch 190 is a reference region corresponding to the portion of the sensor 182 immersed in the fluid. In another embodiment, instead of having notches in the reference portion 184, both the reference portion 184 and the torsional portion 186 may include different material. In other words, the reference portion 184 may include a first material and the torsional portion 186 may include a second material. The exemplary sensor arrangement is also applicable for detection of other parameters of the fluid mixture. The sensor arrangement is also applicable for any single-phase fluid, two-phase fluid mixture, and multi-phase fluid mixture Referring to FIG. 27, a front view of an exemplary torsional sensor 192 is illustrated. The sensor 192 includes a reference portion 194 and a torsional portion 196. In the illustrated embodiment, the reference portion 194 includes a notches or groove 195 for dividing the reference portion 194 into two sub-sections 196. The reference portion 194 and the torsional portion 196 include same material.

In the illustrated embodiment, the torsional portion 196 and a portion of the reference portion 196 with the notch 195 is immersed in the fluid medium. It should be noted herein that any variation in time of flight of the torsional wave along the torsional sensor 192 is attributed to change in at least one parameter of the fluid, for example viscosity. In the illustrated embodiment, the time of flight of the propagation wave is calibrated for a particular viscosity and the time of flight is corrected based on the calibration for determining at least one parameter of the fluid. In another embodiment, instead of having the notch 195 in the reference portion 194, both the reference portion 194 and the torsional portion 196 may include different material. In other words, the reference portion 194 may include a first material and the torsional portion 196 may include a second material.

As discussed with reference to the embodiments discussed above, the shaped of the sensor provides resistance to the propagating torsional wave in the presence of the fluid surrounding the torsional portion. This resistance manifests in the change in time of flight of the propagating wave. The exemplary sensor shape and arrangement provides drag to the propagating wave and increases the time of flight resulting in enhanced resolution of the sensor for measuring one or more parameters of the fluid.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A torsional sensor for sensing at least one parameter of a fluid, the torsional sensor comprising:
 a reference portion; and
 a torsional portion coupled to the reference portion and comprising a plurality of projections extending outward and spaced apart from each other; wherein the torsional portion comprises a plurality of notches dividing the torsional portion into a plurality of torsional sub-sections;
 wherein at least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid.

2. The torsional sensor of claim 1, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid.

3. The torsional sensor of claim 2, wherein the torsional sensor is configured for sensing at least one parameter of a single-phase fluid, or a two-phase fluid mixture, or a multi-phase fluid mixture.

4. The torsional sensor of claim 2, wherein the torsional portion comprises a plurality of individual projections extending outward from a center section and spaced apart from each other.

5. The torsional sensor of claim 4, wherein the plurality of individual projections are disposed symmetrically about the center section of the torsional portion.

6. The torsional sensor of claim 4, wherein the plurality of individual projections are disposed asymmetrically about the center section of the torsional portion.

7. The torsional sensor of claim 4, wherein the torsional portion comprises an X-shaped torsional portion, a star shaped torsional portion, a fan shaped torsional portion, a curved fan shaped torsional portion, or combinations thereof.

8. The torsional sensor of claim 1, wherein the torsional portion has an aspect ratio of 1:2 to 1:7.

9. A sensing system for sensing at least one parameter of a fluid, the sensing system comprising:
 a torsional sensor comprising a reference portion; and a torsional portion coupled to the reference portion and comprising a plurality of projections extending outward and spaced apart from each other; wherein the torsional portion comprises a plurality of notches dividing the torsional portion into a plurality of torsional sub-sections;
 an excitation device configured to excite a shear wave energy in the torsional sensor; wherein at least a portion of the torsional sensor is mountable for immersion in the fluid and operable to propagate the wave energy that interacts with the fluid along the at least portion of the torsional sensor so as to affect propagation of the wave energy in a manner dependent on the at least one parameter of the fluid;
 a transducer device configured to provide shear excitation to the torsional sensor and detect wave energy from the torsional portion;
 a processor device configured to determine at least one parameter of the fluid in response to an output from the transducer device.

10. The sensing system of claim 9, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid.

11. The sensing system of claim 10, wherein the torsional sensor is configured for sensing at least one parameter of a single-phase fluid, or a two-phase fluid mixture, or a multi-phase fluid mixture.

12. The sensing system of claim 10, wherein the torsional portion comprises a plurality of individual projections extending outward from a center section and spaced apart from each other.

13. The sensing system of claim 12, wherein the plurality of individual projections are disposed symmetrically about the center section of the torsional portion.

14. The sensing system of claim 12, wherein the plurality of individual projections are disposed asymmetrically about the center section of the torsional portion.

15. The sensing system of claim 12, wherein the torsional portion comprises an X-shaped torsional portion, a star shaped torsional portion, a fan shaped torsional portion, a curved fan shaped torsional portion, or combinations thereof.

16. The sensing system of claim 10, further comprising another torsional sensor; wherein the one torsional sensor and the other torsional sensor are disposed at different locations in a conduit.

17. The sensing system of claim 16, wherein the one torsional sensor is disposed proximate to one side of a wall of the conduit and the other torsional sensor is disposed between the one torsional sensor and another side of the wall of the conduit.

18. The sensing system of claim 17, wherein the one torsional sensor is configured to detect at least one parameter of one fluid of a two-phase fluid mixture, and the other torsional sensor is configured to detect at least one parameter of another fluid of the two-phase fluid mixture.

19. The sensing system of claim 10, wherein the wave energy from each torsional sub-section is representative of at least one parameter associated with the fluid confined to a corresponding area in a conduit.

20. The sensing system of claim 10, wherein the torsional sensor is disposed extending across a diameter of a conduit.

21. The sensing system of claim 20, wherein the torsional sensor is configured to detect at least one parameter of a single-phase fluid, or a two-phase fluid mixture, or a multi-phase fluid mixture.

22. The sensing system of claim 21, wherein the torsional sensor is configured to detect density of the single-phase fluid, or an average density of the two-phase fluid mixture, or a level of each fluid phase of the multi-phase fluid mixture, or a fraction of each fluid phase of the multi-phase fluid mixture.

23. The sensing system of claim 20, further comprising another torsional sensor; wherein the one torsional sensor and the other torsional sensor are spaced apart by a predetermined distance in the conduit.

24. The sensing system of claim 23, wherein the processor device is configured to determine at least one parameter of the fluid based on difference in output response time of the torsional sensors representative of the wave energy, and the predetermined distance.

25. The sensing system of claim 10, further comprising another torsional sensor, wherein the one torsional sensor has a first length and the other torsional sensor has a second length different from the first length and are disposed at a same location in a conduit.

26. The sensing system of claim 10, comprising a plurality of torsional sensors disposed spaced apart from each other along a cross-section of a conduit.

27. The sensing system of claim 9, wherein the reference portion comprises an enlarged top portion having a recessed side portion; wherein the transducer device is mounted in the recessed side portion.

28. The sensing system of claim 9, wherein the reference portion comprises an enlarged top portion, wherein the transducer device is wrapped around the enlarged top portion.

29. A torsional sensor for sensing at least one parameter of a fluid, the torsional sensor comprising:
a reference portion comprising at least one notch; and
a torsional portion coupled to the reference portion and comprising a plurality of projections extending outward and spaced apart from each other;
wherein at least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid; wherein variation in time of flight of the torsional wave is attributed to change in at least one parameter of the fluid.

30. The torsional sensor of claim 29, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid.

31. The torsional sensor of claim 30, wherein the torsional sensor is configured for sensing at least one parameter of a single-phase fluid, or two phase fluid mixture, or multi-phase fluid mixture.

32. The torsional sensor of claim 30, wherein the torsional portion comprises a plurality of individual projections extending outward from a center section and spaced apart from each other.

33. The torsional sensor of claim 32, wherein the plurality of individual projections are disposed symmetrically about the center section of the torsional portion.

34. The torsional sensor of claim 32, wherein the plurality of individual projections are disposed asymmetrically about the center section of the torsional portion.

35. The torsional sensor of claim 33, wherein the torsional portion comprises an X-shaped torsional portion, a star shaped torsional portion, a fan shaped torsional portion, a curved fan shaped torsional portion, or combinations thereof.

36. A torsional sensor for sensing at least one parameter of a fluid, the torsional sensor comprising:

a reference portion comprising a first material; and
a torsional portion coupled to the reference portion and comprising a plurality of projections extending outward and spaced apart from each other; wherein the torsional portion comprises a second material different from the first material; wherein the torsional portion comprises a plurality of notches dividing the torsional portion into a plurality of torsional sub-sections;
wherein at least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid; wherein variation in time of flight of the torsional wave along the torsional sensor is attributed to change in at least one parameter of the fluid.

37. A torsional sensor for sensing at least one parameter of a fluid, the torsional sensor comprising:
a reference portion comprising at least one notch dividing the reference portions into two or more sub-sections; and
a torsional portion coupled to the reference portion and comprising a plurality of projections extending outward and spaced apart from each other; wherein the reference portion and the torsional portion comprises same material;
wherein at least a portion of the torsional sensor is mountable for immersion in the fluid and operable to propagate a torsional wave that interacts with the fluid along the at least portion of the torsional sensor so as to affect propagation of the torsional wave in a manner dependent on the at least one parameter of the fluid; wherein variation in time of flight of the torsional wave along the torsional sensor is attributed to change in at least one parameter of the fluid.

38. A method for sensing at least one parameter of a fluid, the method comprising:
exciting a wave energy in a torsional sensor partially immersed in the fluid via an excitation device so as to propagate the wave energy that interacts with the fluid along at least a portion of the torsional sensor so as to affect propagation of the wave energy in a manner dependent on the at least one parameter of the fluid, wherein the torsional sensor comprises a reference portion; and a torsional portion coupled to the reference portion and comprising a plurality of projections extending outward and spaced apart from each other; wherein the torsional portion comprises a plurality of notches dividing the torsional portion into a plurality of torsional sub-sections;
providing torsional excitation to the torsional sensor and detecting wave energy from the torsional portion via a transducer device;
determining at least one parameter of the fluid in response to an output from the transducer device.

39. The method of claim 38, comprising sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the fluid.

40. The method of claim 39, comprising sensing at least one parameter of a single-phase fluid, or a two-phase fluid mixture, or a multi-phase fluid mixture.

41. The method of claim 38, comprising exciting the wave energy in the torsional sensor comprising the torsional portion having a plurality of individual projections extending outward from a center section and spaced apart from each other.

42. The method of claim 41, comprising exciting the wave energy in the torsional sensor comprising the plurality of individual projections disposed symmetrically about the center section of the torsional portion.

43. The method of claim 41, comprising exciting the wave energy in the torsional sensor comprising the plurality of individual projections disposed asymmetrically about the center section of the torsional portion.

44. The method of claim 41, comprising exciting the wave energy in the torsional sensor comprising the torsional portion comprising an X-shaped torsional portion, a star shaped torsional portion, a fan shaped torsional portion, a curved fan shaped torsional portion, or combinations thereof.

* * * * *

UNITED STATES PATENT AND TRADEMARK OFFICE
CERTIFICATE OF CORRECTION

| | | |
|---|---|---|
| PATENT NO. | : 8,511,144 B2 | Page 1 of 1 |
| APPLICATION NO. | : 12/685388 | |
| DATED | : August 20, 2013 | |
| INVENTOR(S) | : Goravar et al. | |

It is certified that error appears in the above-identified patent and that said Letters Patent is hereby corrected as shown below:

In the Specification

In Column 5, Line 59, delete "portion" and insert -- portion. --, therefor.

In Column 6, Line 3, delete "portion" and insert -- portion. --, therefor.

In Column 6, Line 10, delete "portion" and insert -- portion. --, therefor.

In Column 10, Line 45, delete "multi-phase fluid mixture" and insert -- multi-phase fluid mixture. --, therefor.

Signed and Sealed this
Fifth Day of November, 2013

Teresa Stanek Rea
*Deputy Director of the United States Patent and Trademark Office*